United States Patent
Lai

(10) Patent No.: US 9,121,598 B2
(45) Date of Patent: Sep. 1, 2015

(54) ELECTRONIC INCENSE ASSEMBLY

(71) Applicant: HON HAI PRECISION INDUSTRY CO., LTD., New Taipei (TW)

(72) Inventor: Chih-Chen Lai, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 198 days.

(21) Appl. No.: 13/912,214

(22) Filed: Jun. 7, 2013

(65) Prior Publication Data

US 2014/0184084 A1 Jul. 3, 2014

(30) Foreign Application Priority Data

Dec. 28, 2012 (TW) .............................. 101150818 A

(51) Int. Cl.
| | |
|---|---|
| *H05B 37/02* | (2006.01) |
| *F21V 33/00* | (2006.01) |
| *F21S 6/00* | (2006.01) |
| *F21V 23/04* | (2006.01) |
| *F21V 8/00* | (2006.01) |
| *H05B 37/00* | (2006.01) |
| *A61L 9/03* | (2006.01) |
| *F21W 121/00* | (2006.01) |
| *F21Y 101/02* | (2006.01) |

(52) U.S. Cl.
CPC ............ *F21V 33/0028* (2013.01); *F21S 6/001* (2013.01); *F21V 23/0442* (2013.01); *F21V 23/0478* (2013.01); *G02B 6/0008* (2013.01); *H05B 37/00* (2013.01); *H05B 37/029* (2013.01); *A61L 9/03* (2013.01); *A61L 2209/12* (2013.01); *F21W 2121/00* (2013.01); *F21Y 2101/02* (2013.01); *Y10S 362/806* (2013.01)

(58) Field of Classification Search
None
See application file for complete search history.

(56) References Cited

U.S. PATENT DOCUMENTS

| | | | | |
|---|---|---|---|---|
| 6,447,732 | B1 * | 9/2002 | West | 422/126 |
| 8,298,489 | B1 * | 10/2012 | Chen | 422/126 |
| 8,313,225 | B1 * | 11/2012 | Chen | 362/565 |
| 2007/0195548 | A1 * | 8/2007 | Wang | 362/555 |
| 2013/0163275 | A1 * | 6/2013 | Chen | 362/562 |
| 2013/0171032 | A1 * | 7/2013 | Chen | 422/126 |
| 2014/0167625 | A1 * | 6/2014 | Tseng | 315/158 |

* cited by examiner

*Primary Examiner* — Tuan T Lam

(74) *Attorney, Agent, or Firm* — Novak Druce Connolly Bove + Quigg LLP

(57) ABSTRACT

An electronic incense assembly includes a burning chamber, an electronic stick, a camera module, an image processor and a controller. The burning chamber includes a sidewall. The electronic stick is positioned on the burning chamber, and includes a light guide bar and a light source. The light guide bar includes a first end and a second end away from the first end. The light source is positioned on the second end. The camera module is positioned on the sidewall. The image processor includes an environment brightness sensor. The controller is electrically connected to the camera module and the image processor. The environment brightness sensor is configured to sense an environment brightness based on a captured image captured by the camera module. The controller is configured to receive the environment brightness and to drive the light source to emit suitable light according to the environment brightness.

13 Claims, 2 Drawing Sheets

ELECTRONIC INCENSE ASSEMBLY

BACKGROUND

1. Technical Field

The present disclosure relates to an electronic incense assembly.

2. Description of Related Art

Electronic incense sticks typically include a transparent tube having an opened end and a bulb portion at an opposite end of the tube, non-transparent coatings on an outer surface of the tube to simulate an incense coating and a bone part of traditional incense sticks, and a light emitting diode (LED) positioned at the opened end. The LED emits light, which is directed to the bulb portion via multiple internal reflections on an inner surface of the tube. Thus, the electronic incense stick appears to burn. However, the electronic incense sticks are not vivid in morphology in comparison to the traditional incense sticks.

Therefore, it is desirable to provide an electronic incense stick which can overcome the above-mentioned limitations.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure.

DETAILED DESCRIPTION

Figure 1:
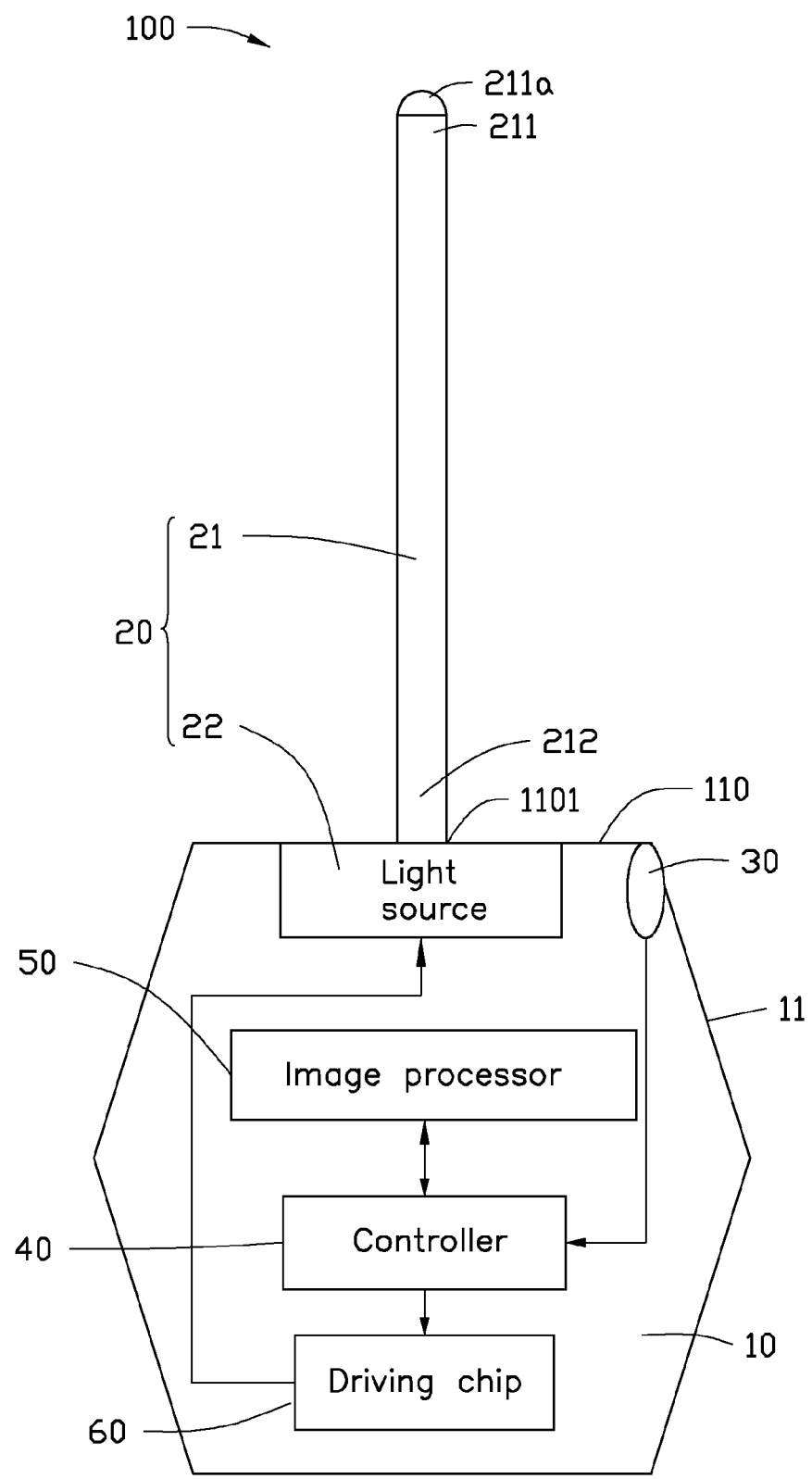
FIG. 1 is a schematic view of an electronic incense assembly including an image processor according to an embodiment.

FIG. 1 shows an electronic incense assembly 100, according to an embodiment. The electronic incense assembly 100 includes a burning chamber 10, a electronic stick 20 positioned on the burning chamber 10, a camera module 30, a controller 40, an image processor 50 and a driving chip 60.

The burning chamber 10 is a hollow chamber for receiving the camera module 30, the controller 40, the image processor 50 and the driving chip 60. In the embodiment, the electronic stick assembly 100 also includes a cover 110 for the burning chamber 11. The cover 110 defines a through hole 1101.

The electronic stick 20 includes a light guide bar 21 and a light source 22. The light guide bar 21 includes a first end 211 and a second end 212 away from the first end 211. The second end 212 runs through the through hole 1101 to position the light guide bar 21 on the cover 110. A glowing head 211a is positioned at the first end 211. A roughness of the glowing head 211a is larger than the roughness of the first end 211. In the embodiment, the glowing head 211a is the polished region by fine grinding method. Therefore, the glowing head 211a is capable of simulating the incandescent glowing tip of traditional incense sticks, when the electronic stick assembly 100 is used. In particular, the glowing head 211a is a bullet shape created by a grinding method.

The light guide bar 21 is configured to simulate incense coating of traditional incense sticks. Accordingly, the light guide bar 21 can have a yellow or red color. In particular, the light guide bar 21 has a thermoplastic property.

The light source 22 is positioned on the second end 212 of the light guide bar 21. The light source 22 can be a lamp or a light emitting diode and configured for emitting light.

In use, the light source 22 emits a highly collimated light beam into the light guide bar 21, which transmits to the glowing head 211a along a central axis of the light guide bar 21. Then, the light beam is diffused by the glowing head 211a. As such, the electronic stick 20 appears burning-like.

The camera module 30 is positioned on a sidewall 11 of the burning chamber 10.

The controller 40 is electrically connected to the camera module 30, the image processor 50 and the driving chip 60. The controller 40 is configured to transmit images captured by the camera module 30 into the image processor 50.

Figure 2:
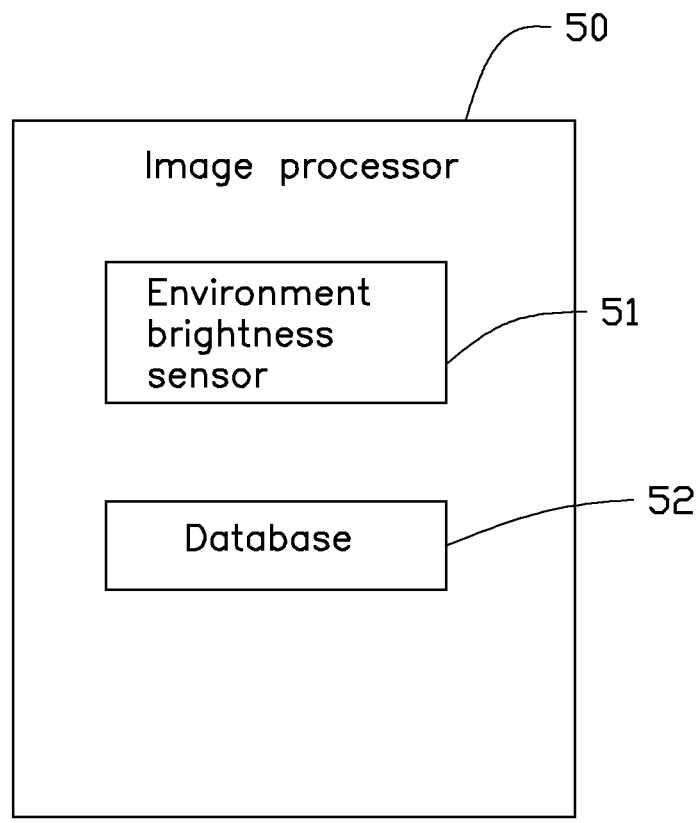
FIG. 2 is a function block diagram of the image processor of FIG. 1.

Referring to FIG. 2, the image processor 50 includes an environment brightness sensor 51 and builds a database 52 about prayer actions, such as prayer or kowtow. The environment brightness sensor 51 is configured to sense an environment brightness based on a captured image captured by the camera module 30.

The controller 40 is configured to receive the environment brightness and to drive the light source 22 to emit suitable light according to the environment brightness. In particular, the controller 40 controls the camera module 30 to capture an image at every predetermined time, such as 60-100 seconds. The environment brightness sensor 51 senses the environment brightness based on the captured image captured by the camera module 30. When the environment brightness is higher than the light brightness of the light emitted by the light source 22, the controller 40 controls the driving chip 60 to drive the light source 22 to heighten the light brightness until the light brightness of the light emitted by the light source 22 is higher than the environment brightness.

When a user prays, the camera module 30 captures images of the user, the controller 40 transmits images captured by the camera module 30 into the image processor 50. The image processor 50 detects that the user's actions match with the prayer actions built in the database 52, then the controller 40 identifies the user's prayer action according to the image processor 50 detected, and controls the driving chip 60 to make the light source 22 flash, to achieve interactive effect.

It will be understood that the above particular embodiments are shown and described by way of illustration only. The principles and the features of the present disclosure may be employed in various and numerous embodiment thereof without departing from the scope of the disclosure as claimed. The above-described embodiments illustrate the possible scope of the disclosure but do not restrict the scope of the disclosure.

What is claimed is:

1. An electronic incense assembly, comprising:
   a burning chamber comprising a sidewall;
   an electronic stick positioned on the burning chamber, and comprising a light guide bar and a light source, the light guide bar comprising a first end and a second end opposite to the first end, the light source positioned on the second end;
   a camera module positioned on the sidewall;
   a image processor comprising an environment brightness sensor; and
   a controller electrically connected to the camera module and the image processor;
   wherein the controller is configured to transmit images captured by the camera module to the image processor, the environment brightness sensor is configured to sense an environment brightness based on a captured image captured by the camera module, the controller is configured to receive the environment brightness and to drive the light source to emit suitable light according to the environment brightness.

2. The electronic incense assembly of claim 1, comprising a cover for covering the burning chamber, wherein the cover defines a through hole, the second end runs through the through hole to position the light guide bar on the cover.

3. The electronic incense assembly of claim 1, wherein the light guide bar comprises a glowing head positioned at the first end.

4. The electronic incense assembly of claim 3, wherein a roughness of the glowing head is larger than a roughness of the first end.

5. The electronic incense assembly of claim 3, wherein the glowing head is a polished region by fine grinding method.

6. The electronic incense assembly of claim 3, wherein the glowing head is in a bullet shape.

7. The electronic incense assembly of claim 1, wherein the light guide bar has is yellow or red.

8. The electronic incense assembly of claim 1, wherein the light guide bar has a thermoplastic property.

9. The electronic incense assembly of claim 1, wherein the light source is a light emitting diode.

10. The electronic incense assembly of claim 1, wherein the controller controls the camera module to capture an image at each predetermined time period.

11. The electronic incense assembly of claim 1, comprising a driving chip, wherein the driving chip is electrically connected to the light source and also electrically connected to the controller.

12. The electronic incense assembly of claim 11, wherein when the environment brightness is higher than a light brightness of the light emitted by the light source, the controller controls the driving chip to drive the light source to heighten the light brightness until the light brightness of the light emitted by the light source is higher than the environment brightness.

13. The electronic incense assembly of claim 11, wherein the image processor builds a database about prayer actions, when the camera module captures images of a user, the controller transmits the images captured by the camera module to the image processor, the image processor detects that the user's actions match with the prayer actions built in the database, then the controller identifies the user's prayer action according to the image processor's detection and controls the driving chip to make the light source flash.

* * * * *